United States Patent [19]

Akasaki et al.

[11] Patent Number: 5,011,969
[45] Date of Patent: Apr. 30, 1991

[54] FLUORENE DERIVATIVE AND PROCESS FOR PREPARATION THEREOF

[75] Inventors: Yutaka Akasaki; Katsumi Nukada; Katsuhiro Sato, all of Kanagawa, Japan

[73] Assignee: Fuji Xerox Co., Ltd., Tokyo, Japan

[21] Appl. No.: 436,880

[22] Filed: Nov. 16, 1989

[30] Foreign Application Priority Data

Nov. 16, 1988 [JP] Japan .................. 63-287614

[51] Int. Cl.$^5$ .......................................... C07C 255/50
[52] U.S. Cl. ...................... 558/402; 558/374; 558/405
[58] Field of Search ............. 558/402, 405, 374

[56] References Cited

U.S. PATENT DOCUMENTS 4,833,263  5/1989  Akasaki et al. ............. 558/374

FOREIGN PATENT DOCUMENTS 0912019  10/1972  Canada ..................... 558/374
489988   3/1973   Japan ...................... 558/405
5430834  3/1979   Japan ...................... 558/405

*Primary Examiner*—Mary C. Lee
*Assistant Examiner*—J. Richter
*Attorney, Agent, or Firm*—Finnegan, Henderson, Farabow, Garrett, and Dunner

[57] ABSTRACT

Fluorene derivatives represented by the general formula (I):

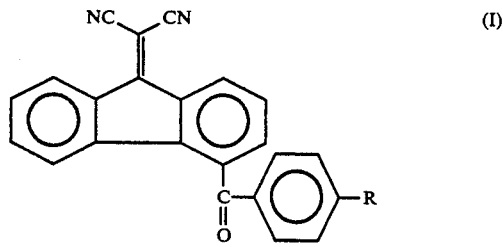

wherein R represents an alkyl group having 1 to 8 carbon atoms, a phenyl group of a $C_1$–$C_8$ alkyl-substituted phenyl group, and a process for preparation thereof. These fluorene derivatives are synthesized by reacting fluorenone derivatives represented by the general formula (II):

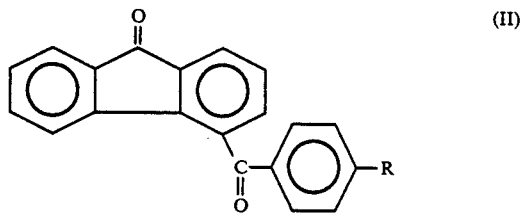

wherein R is the same as defined above, with malonitrile.

2 Claims, No Drawings

FLUORENE DERIVATIVE AND PROCESS FOR PREPARATION THEREOF

FIELD OF THE INVENTION

The present invention relates to novel fluorene derivatives which are useful in electrophotographic light-sensitive material, and a process for the preparation thereof.

BACKGROUND OF THE INVENTION

Electrophotographic photoreceptors using an organic photoconductive substance have been extensively studied because of advantages such as no pollution, high productivity and low production cost. An electrophotographic photoreceptor containing a diphenyldicyanoethylene derivative as a sensitizer in a light-sensitive layer thereof is known as described in, for example, JP-A-54-30834 (the term "JP-A" as used herein means an "unexamined published Japanese patent application").

An organic photoconductive substance which generates an electric charge upon absorption of visible light is poor in electric charge-retaining force. Conversely, an organic photoconductive substance which is good in electric charge-retaining force and excellent in film-forming properties generally does not exhibit any substantial photoconductivity upon application of visible light. In order to overcome the above problem, a laminate type light-sensitive layer has been designed, i.e., a layer structure that is functionally separated into an electric charge-generating agent which generates an electric charge upon absorption of visible light and an electric charge-transporting agent which transports an electric charge. A number of electric charge-generating agents and electric charge-transporting agents have been proposed. Known positive hole-transporting agents include amine compounds, hydrazone compounds, pyrazoline compounds, oxazole compounds, oxadiazole compounds, stilbene compounds, carbazole compounds and the like, and known electron-transporting agents include 2,4,7-trinitrofluorenone and the like. In addition, boron-containing compounds are described, for example, as a photoconductive substance in JP-B-48-9988 (the term "JP-B" as used herein means an "examined Japanese patent publication"), and as a fluorescent agent in Canadian Pat. No. 912,019.

A sensitizer, which is sufficient for use with an electrophotographic photoreceptor of a single layer structure using an organic photoconductive substance has not been known in the art. A positive charging type material is desirable for use in a function separation type electrophotographic photoreceptor of the laminate structure for preventing generation of ozone in corotron and for controlling charging of a toner in development. In the case of the positive charging type material, when the electric charge-transporting agent is positive hole-transporting, it is necessary for the electric charge-generating layer to be provided as an upper layer. The electric charge-generating layer is usually made thin in view of its function and fails to sufficiently satisfy mechanical characteristics as a photoreceptor. Moreover, some modifications should be made to a copying machine, to use it in a negative charging system. Thus a positive charging type photoreceptor having a relatively thick electric charge-transporting layer as an upper layer is desired, and in this case, it is necessary to use an electron-transporting electric charge-transporting agent in the electric charge-transporting layer. However, of electron-transporting electric charge-transporting agents conventionally proposed, no sufficiently satisfactory substance has been known.

SUMMARY OF THE INVENTION

An object of the present invention is to provide an organic photoconductive substance which is useful as an electric charge-transporting agent in a positive charging laminate-type electrophotographic photoreceptor.

It has now been found that a group of fluorene derivatives are useful as electric charge-transporting agents.

The present invention relates to a fluorene derivative represented by formula (I):

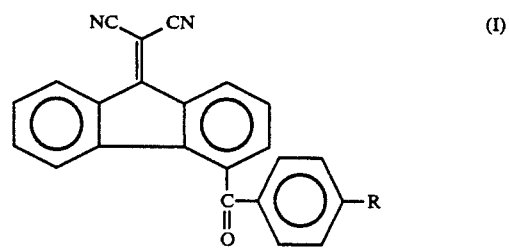

wherein R represents an alkyl group having 1 to 8 carbon atoms, a phenyl group or a $C_1$-$C_8$ alkyl-substituted phenyl group.

The present invention further relates to a process for preparing a fluorene derivative represented by formula (I) which comprises reacting a fluorenone derivative represented by the following formula (II) with malonitrile:

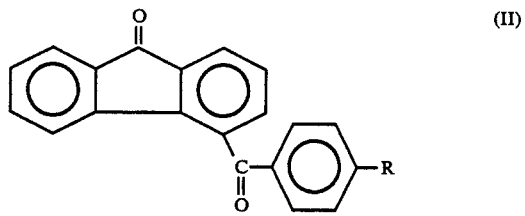

wherein R is the same as defined above.

DETAILED DESCRIPTION OF THE INVENTION

Examples of the fluorene derivatives represented by formula (I) are shown below.

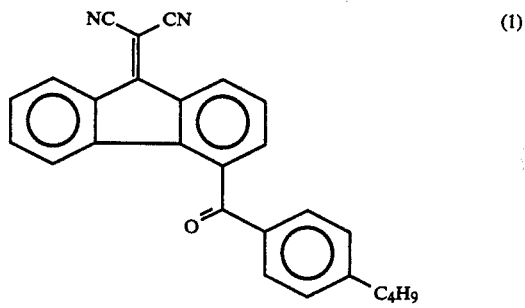

-continued

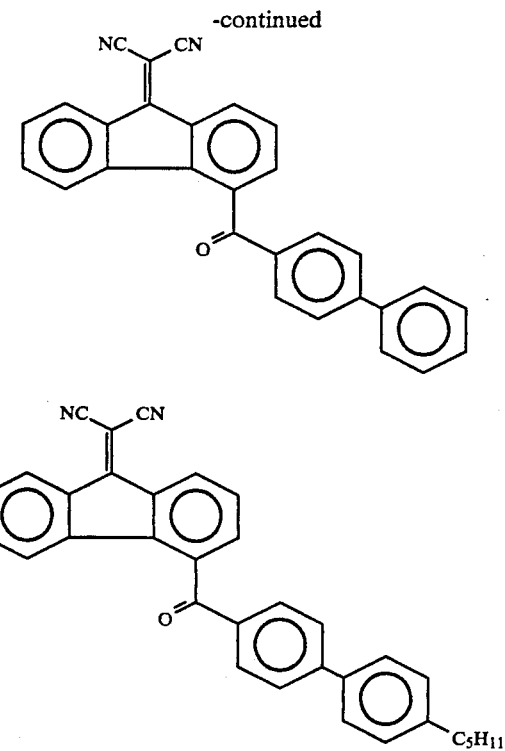

The alkyl group and the alkyl moiety of the alkyl-substituted phenyl group of R preferably have 1 to 5 carbon atoms.

The fluorene derivatives represented by formula (I) of the present invention can be prepared by heating under reflux fluorenone derivatives represented by formula (II) and malonitrile in a solvent, e.g., pyridine.

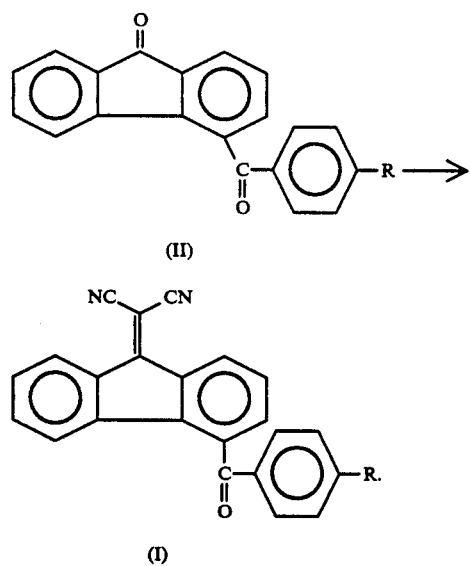

The fluorenone compounds represented by formula (II) can be synthesized, as illustrated by the reaction scheme shown below, by reacting fluorenonecarboxylic acid and thionyl chloride to prepare an acid chloride represented by formula (III) and reacting the acid chloride obtained above with alkylbenzene, biphenyl or alkylbiphenyl in a solvent such as methylene chloride:

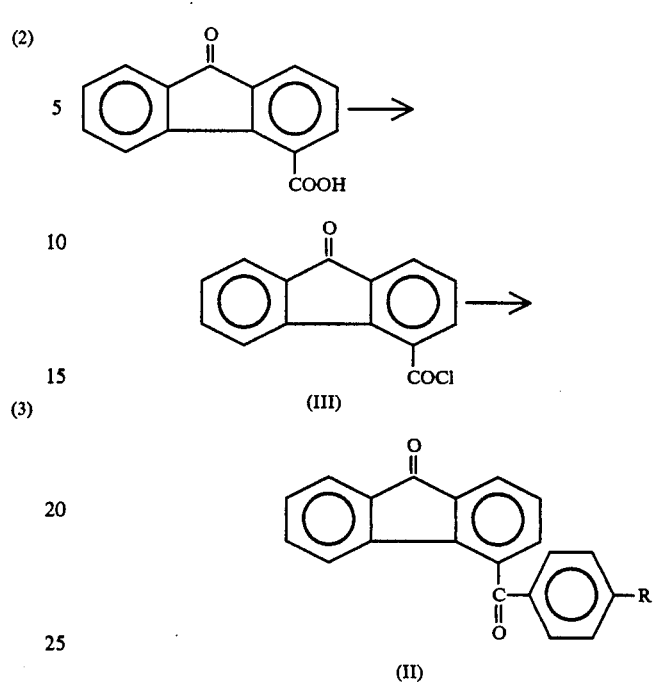

wherein R is the same as defined above.

In the present invention, suitable alkylbenzenes which are reacted with the above acid chloride include methylbenzene, ethylbenzene, butylbenzene, o-xylene, and o-butyltoluene. Suitable the alkylbiphenyls include 4-methylbiphenyl, 4-ethylbiphenyl, 4-pentylbiphenyl and the like.

The fluorene derivatives represented by formula (I) of the present invention exhibit excellent electron-transporting properties and when used as a sensitizer or an electric charge-transporting agent for an electrophotographic photoreceptor, can provide a positive charging electrophotographic photoreceptor exhibiting excellent electrophotographic characteristics.

The fluorene derivatives represented by formula (I) of the present invention exhibit electron-transporting properties superior to those of 2,4,7-trinitrofluorenone conventionally known to be relatively good, and thus are useful as a sensitizer or an electric charge-transporting agent for a positive charging type electrophotographic photoreceptor. For example, if after providing an electric charge-generating layer on an electrically conductive support, an electric charge-transporting layer is formed by coating the above fluorene derivative with a film-forming resin, there is obtained a positive charging type electrophotographic photoreceptor having excellent electrophotographic characteristics.

The present invention is described in greater detail with reference to the following examples.

EXAMPLE 1

25.0 g (111 mmol) of 9-fluorenone-4-carboxylic acid and 300 mλ of thionyl chloride were placed in a 500 mλ three-necked flask and refluxed in a stream of nitrogen for 5 hours. Then the thionyl chloride was distilled away under reduced pressure, and 100 mλ of 1,2-dichloroethane was added to the resulting residue and distilled away under reduced presure to remove the remaining thionyl chloride. To the acid chloride thus formed was added 200 mλ of methylene chloride. After cooling to −20° C. in a cooling bath, 20.0 g (150 mmol)

of aluminum chloride was added and the resulting mixture was stirred in a stream of nitrogen for 15 hours. Then, a solution comprising 15.9 g (118 mmol) of n-butylbenzene and 50 mλ of methylene chloride was dropped over 30 minutes. After the completion of dropping, stirring was continued for 3 hours, and after removing from the cooling bath, stirring was continued at room temperature for 20 hours. Moreover, 7.5 g of (56.3 mmol) of aluminum chloride was added, stirred for 2.5 hours and then poured onto 150 g of ice. A 20% potassium hydroxide solution was added until aluminum hydroxide was dissolved, and an organic layer was separated. An aqueous layer was extracted with methylene chloride, and the organic layers obtained were combined and the solvent was distilled away under reduced pressure. To the resulting residue was added 200 mλ of 5% potassium hydroxide, and the resulting mixture was heated at 80° C. to decompose the remaining acid chloride. Then the product was extracted with methylene chloride. After purification on a silica gel short column (elution with methylene chloride) and distillation of the solvent, the product was recrystallized from hexane and then from ethyl acetate to obtain 13.8 g of 4-(4'-n-butyl-phenylcarbonyl)fluorene-9-one as a yellow powder (yield 36.4 %). M.p., 93–95° C. Infrared absorption spectrum: 1726, 1720 cm$^{-1}$ (C=O)(KBr)

6.5 g of the fluorenone derivative obtained, 1.3 g of malonitrile, 5 drops of piperidine and 80 mλ of methanol were placed in a 100 mλ three-necked flask and refluxed in a stream of nitrogen for 2 hours. The mixture was cooled to room temperature, and the precipitated crystals were filtered off, washed with methanol, water and then with methanol, and then recrystallized from methanol/CH$_2$Cl$_2$ to obtain 5 g of the objective fluorene compound (Illustrative Compound (1)) as orange fibrous crystals (yield 68%).

M.p., 156–157° C.

Mass spectral analysis: M$^{30}$ 388.

UV absorption spectrum: $\lambda_{max}$: 259 nm, 351 nm, 366 nm (in CH$_2$Cl$_2$).

Infrared absorption spectrum: 2224 cm$^{-1}$ (KBr).

EXAMPLE 2

In the same manner as in Example 1 except that biphenyl was used in place of n-butylbenzene in the same amount, the objective fluorene compound (Illustrative Compound (2) (R=phenyl group in formula (I)) was obtained as orange fibrous crystals.

M.p., 229–230.5° C.

| Elemental analysis: | | | |
|---|---|---|---|
| | C | H | N |
| Calculated | 85.28 | 3.95 | 6.86 |
| Found | 85.44 | 3.68 | 6.66 |

Mass spectral analysis: M$^{30}$ 408.

UV absorption spectrum: $\lambda_{max}$: 262 nm, 300 nm, 353 nm, 369 nm, (in CH$_2$Cl$_2$).

Infrared absorption spectrum: 2224 cm$^{-1}$ (KBr).

EXAMPLE 3

In the same manner as in Example 1 except that pentylbiphenyl was used in place of n-butylbenzene in the same amount, the objective fluorene compound (Illustrative Compound (3)) (R=pentylphenyl group in formula (I)) was obtained as orange fibrous crystals.

M.p., 171–172° C.

| Elemental analysis: | | | |
|---|---|---|---|
| | C | H | N |
| Calculated | 85.33 | 5.48 | 5.83 |
| Found | 85.45 | 5.30 | 5.80 |

Mass spectral analysis: M$^{30}$ 478.

UV absorption spectrum: $\lambda_{max}$: 262 nm, 300 nm, 353 nm, 369 nm (in CH$_2$Cl$_2$).

Infrared absorption spectrum: 2220 cm$^{-1}$ (KBr).

APPLICATION EXAMPLE 1

An electric charge-generating layer (2.5 μm) comprising trigonal selenium/polyvinyl carbazole (trigonal selenium 7% by volume) was provided on an electrically conductive substrate, and on the electric charge-generating layer, a solution of 0.5 g of the fluorene derivative synthesized in Example 1 and 0.75 g of bisphenol A polycarbonate (Makrolon 5705 made by U.S Bayer Co., Ltd.) dissolved in 7 g of methylene chloride was coated in a 5 mil of gap at the time of wetting and dried at 80° C. for 1 hour to produce an electrophotographic photoreceptor. This electro-photographic photoreceptor was charged at +800 V and −800 V bY the use of an electrostatic copying paper tester (SP428 produced by Kawaguchi Denki Seisakusho Co., Ltd.) and exposed to 5 lux white light to measure sensitivity (dV/dt).

| Charged potential | +800 V | −800 V |
|---|---|---|
| Initial sensitivity (V/sec) | 2015 | — |

APPLICATION EXAMPLES 2 AND 3

In the same manner as in Application Example 1 except that the fluorene derivatives synthesized in Examples 2 and 3 were used in place of the fluorene derivative synthesized in Example 1, electrophotographic photoreceptors were prepared, and measured for sensitivity. The results are shown in Table 1.

COMPARATIVE EXAMPLE

In the same manner as in Example 1 except that 2,4,7-trinitrofluorenone (TNF) was used in place of the fluorene derivative synthesized in Example 1, an electrophotographic photoreceptor was prepared and measured for sensitivity. The results are shown in Table 1.

TABLE 1

| | Initial Sensitivity | |
|---|---|---|
| | +800 V | −800 V |
| Application Example 2 | 1215 | — |
| Application Example 3 | 1930 | — |
| Comparative Example | 66 | — |

While the invention has been described in detail and with reference to specific examples thereof, it will be apparent to one skilled in the art that various changes and modifications can be made therein without departing from the spirit and scope thereof.

What is claimed is:
1. A fluorene derivative represented by formula (I):
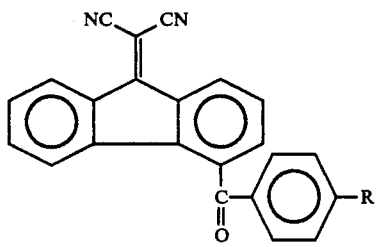 (I)
wherein R represents an alkyl group having 1 to 8 carbon atoms, a phenyl group or a $C_1$–$C_8$ alkyl-subsitiuted phenyl group.
2. The fluorene derivative according to claim 1, wherein R is selected from the group consisting of
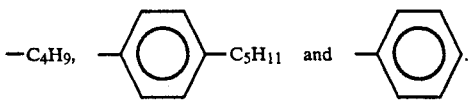
* * * * *

UNITED STATES PATENT AND TRADEMARK OFFICE
CERTIFICATE OF CORRECTION

PATENT NO. : 5,011,969
DATED : April 30, 1991
INVENTOR(S) : Yutaka Akasaki et al.

It is certified that error appears in the above-identified patent and that said Letters Patent is hereby corrected as shown below:

In the Abstract, Line 1, after "derivatives" insert --which are useful in electrophotographic light-sensitive material--;

In the Abstract, Line 5, after "group", change "of" to --or--;

Claim 1, Column 8, Line 2, change "subsitiuted" to --substituted--.

Signed and Sealed this

Ninth Day of February, 1993

Attest:

STEPHEN G. KUNIN

Attesting Officer

Acting Commissioner of Patents and Trademarks